United States Patent
Wamprecht

(10) Patent No.: US 8,367,794 B2
(45) Date of Patent: Feb. 5, 2013

(54) POLYISOCYANATE MIXTURES

(75) Inventor: Christian Wamprecht, Neuss (DE)

(73) Assignee: Bayer MaterialScience AG, Leverkusen (DE)

( * ) Notice: Subject to any disclaimer, the term of this patent is extended or adjusted under 35 U.S.C. 154(b) by 469 days.

(21) Appl. No.: 12/209,326

(22) Filed: Sep. 12, 2008

(65) Prior Publication Data

US 2009/0076228 A1    Mar. 19, 2009

(30) Foreign Application Priority Data

Sep. 14, 2007   (DE) .......................... 10 2007 044 034

(51) Int. Cl.
*C08G 18/16* (2006.01)

(52) U.S. Cl. ................ 528/49; 528/55; 528/56; 528/67; 560/25; 560/345; 560/351; 560/359; 564/44; 564/45; 252/182.21; 252/182.22

(58) Field of Classification Search .................... 528/49, 528/55, 56, 67; 560/25, 345, 351, 359, 26, 560/115; 252/182.21, 182.22; 564/44, 45
See application file for complete search history.

(56) References Cited

U.S. PATENT DOCUMENTS

| | | | | |
|---|---|---|---|---|
| 3,769,318 | A | | 10/1973 | Windemuth et al. |
| 4,115,429 | A | * | 9/1978 | Reiff et al. ..................... 560/351 |
| 4,118,411 | A | | 10/1978 | Reiff et al. |
| 5,319,053 | A | * | 6/1994 | Slack et al. ..................... 528/48 |
| 5,610,260 | A | * | 3/1997 | Schmalstieg et al. ........... 528/49 |
| 6,797,799 | B1 | * | 9/2004 | Slack et al. ..................... 528/60 |
| 2001/0007012 | A1 | * | 7/2001 | Tazzia ............................. 528/56 |
| 2004/0171869 | A1 | * | 9/2004 | Reif et al. ..................... 560/347 |
| 2004/0197570 | A1 | | 10/2004 | Slack et al. |
| 2006/0084776 | A1 | * | 4/2006 | Simon et al. .................... 528/44 |

FOREIGN PATENT DOCUMENTS

| | | |
|---|---|---|
| DE | 4403233 A1 | 8/1995 |
| EP | 0666276 A1 | 8/1995 |
| EP | 1930357 A2 | 6/2008 |
| FR | 2380309 A | 9/1978 |
| GB | 994890 A | 6/1965 |
| WO | WO 2005047361 A1 * | 5/2005 |

* cited by examiner

*Primary Examiner* — Michael L Leonard
(74) *Attorney, Agent, or Firm* — Connolly Bove Lodge & Hutz, LLP

(57) ABSTRACT

The invention relates to liquid polyisocyanate mixtures, to a process for their preparation and to their use in single- and two-component polyurethane coating compositions.

13 Claims, No Drawings

US 8,367,794 B2

POLYISOCYANATE MIXTURES

RELATED APPLICATIONS

This application claims benefit to German Patent Application No. 10 2007 044 034.2, filed Sep. 14, 2007, which is incorporated herein by reference in its entirety for all useful purposes.

BACKGROUND OF THE INVENTION

The invention relates to liquid polyisocyanate mixtures based on diphenylmethane 2,4'-diisocyanate, to a process for their preparation and to their use in single- and two-component polyurethane coating compositions, adhesives and sealants.

Two-component polyurethane coating compositions based on diphenylmethane 4,4'-diisocyanate are known. For instance, EP-A 0 666 276 describes polyisocyanate mixtures which are liquid at temperatures above 5° C. and are based on diphenylmethane 4,4'-diisocyanate with an isocyanate group content of 14.5 to 24% by weight and a content of allophanate groups (calculated as $C_2HN_2O_3$) of 7.7 to 14.5% by weight, and also a process for their preparation. These polyisocyanate mixtures are notable for relatively good crystallization stability and high reactivity in combination with reactants containing hydroxyl groups. In the introductory part of the description of EP-A 0 666 276, it is mentioned that mixtures composed of diphenylmethane 4,4'-diisocyanate and relatively large amounts of diphenylmethane 2,4'-diisocyanate are liquid, but have poor crystallization stability, and that the properties of coating materials produced therefrom deteriorate significantly owing to the proportion of diphenylmethane 2,4'-diisocyanate.

For some applications, however, the use of polyisocyanates based on diphenylmethane 4,4'-diisocyanate is undesirable owing to the high reactivity of this isocyanate. Instead, the demand is for polyisocyanates which, in corresponding applications, have similar material properties to those obtainable on the basis of diphenylmethane 4,4'-diisocyanate, but have lower reactivity and hence a longer processing time.

Owing to the isocyanate group in the 2 position, diphenylmethane 2,4'-diisocyanate has lower reactivity towards isocyanate-reactive reactants than diphenylmethane 4,4'-diisocyanate, but diphenylmethane 2,4'-diisocyanate is solid at room temperature, and polyisocyanates based on diphenylmethane 2,4'-diisocyanate also have poor crystallization stability and usually also high viscosities.

It was therefore an object of the invention to provide novel polyisocyanate mixtures which, compared to those based on diphenylmethane 4,4'-diisocyanate, have lower reactivity and significantly better crystallization stability, even at low temperatures below 5° C. This object is achieved through provision of the polyisocyanate mixtures which have allophanate groups and which are characterized in detail below.

EMBODIMENTS OF THE INVENTION

An embodiment of the present invention is a polyisocyanate mixture which is liquid at temperatures above −5° C. and is based on diphenylmethane 2,4'-diisocyanate, wherein
  A) the NCO content of said polyisocyanate mixture is 14.5 to 24% by weight;
  B) the content of isocyanate groups bonded in the 2 position of said polyisocyanate mixture is greater than 50%; and
  C) the content of allophanate groups (calculated as $C_2HN_2O_3$ having a molecular weight of 101) of said polyisocyanate mixture is 7.7 to 17.6% by weight.

Yet another embodiment of the present invention is an isocyanate-functional prepolymer, a polyurethane dispersion, a polyurethane solution, or a silane-terminated prepolymer comprising the above polyisocyanate mixture as polyisocyanate component.

Yet another embodiment of the present invention is a single- or two-component polyurethane coating composition comprising the above polyisocyanate mixture as polyisocyanate component.

Yet another embodiment of the present invention an adhesive comprising a compound obtained from the above polyisocyanate mixture.

Yet another embodiment of the present invention is a sealant comprising a compound obtained from the above polyisocyanate mixture.

Another embodiment of the present invention is the above polyisocyanate mixture, wherein said polyisocyanate mixture comprises reaction products prepared with intermediate urethane formation from
  A) diphenylmethane 2,4'-diisocyanate with
  B) monohydric alcohols having 3 to 18 carbon atoms per molecule while maintaining an NCO/OH ratio of 4:1 to 8.5:1, Yet another embodiment of the present invention is an isocyanate-functional prepolymer, a polyurethane dispersion, a polyurethane solution, or a silane-terminated prepolymer comprising the above polyisocyanate mixture as polyisocyanate component.

Yet another embodiment of the present invention is a single- or two-component polyurethane coating composition comprising the above polyisocyanate mixture as polyisocyanate component.

Yet another embodiment of the present invention an adhesive comprising a compound obtained from the above polyisocyanate mixture.

Yet another embodiment of the present invention is a sealant comprising a compound obtained from the above polyisocyanate mixture.

Another embodiment of the present invention is the above polyisocyanate mixture, wherein said polyisocyanate mixture comprises reaction products prepared with intermediate urethane formation from
  A) diphenylmethane 2,4'-diisocyanate with
  B) linear, monohydric alcohols having 4 to 10 carbon atoms.

Yet another embodiment of the present invention is an isocyanate-functional prepolymer, a polyurethane dispersion, a polyurethane solution, or a silane-terminated prepolymer comprising the above polyisocyanate mixture as polyisocyanate component.

Yet another embodiment of the present invention is a single- or two-component polyurethane coating composition comprising the above polyisocyanate mixture as polyisocyanate component.

Yet another embodiment of the present invention an adhesive comprising a compound obtained from the above polyisocyanate mixture.

Yet another embodiment of the present invention is a sealant comprising a compound obtained from the above polyisocyanate mixture.

Yet another embodiment of the present invention is a process for preparing a polyisocyanate mixture which is liquid at temperatures between −5 and +5° C. and are based on diphenylmethane 2,4'-diisocyanate, comprising reacting said diphenylmethane 2,4'-diisocyanate with monohydric alcohols having 3 to 18 carbon atoms per molecule while maintaining an NCO/OH ratio of 4:1 to 8.5:1 at temperatures up to 160° C. with intermediate urethane formation, wherein said reaction is carried out no later than after completion of urethane formation in the presence of a catalyst which promotes allophanate formation.

Another embodiment of the present invention is the above process, wherein said catalyst comprises a compound of the third or fourth main group or of transition group 1, 2, 6, 7 or 8 of the Periodic Table of the Elements, and which are soluble in the reaction mixture.

Another embodiment of the present invention is the above process, wherein said catalyst used comprises tin (II) octoate or zinc acetylacetonate.

DESCRIPTION OF THE INVENTION

Here and hereinafter, diphenylmethane 2,4'-diisocyanate represents both the pure 2,4'-isomer and its mixtures with up to 2.0% of diphenylmethane 4,4'-diisocyanate and/or up to 1.0% of diphenylmethane 2,2'-diisocyanate, where the percentages are each based on the overall mixture. The diphenylmethane 2,4'-diisocyanate used as the starting material is preferably composed of at least 98.5% of the 2,4'-isomer.

The invention provides polyisocyanate mixtures which are liquid at temperatures above −5° C. and are based on diphenylmethane 2,4'-diisocyanate, characterized by
A) an NCO content of 14 to 24% by weight, and
B) a content of allophanate groups (calculated as $C_2HN_2O_3$, molecular weight=101) of 7.7 to 17.6% by weight.

The invention also provides a process for preparing these polyisocyanate mixtures, which is characterized in that diphenylmethane 2,4'-diisocyanate is reacted with monohydric alcohols having 3 to 18 carbon atoms per molecule while maintaining an NCO/OH ratio of 4:1 to 8.5:1 at temperatures up to 160° C. with intermediate urethane formation, the reaction being carried out no later than after completion of urethane formation in the presence of a catalyst which promotes allophanate formation.

The invention finally also provides the use of the inventive polyisocyanate mixtures as polyisocyanate component in single- and two-component polyurethane coating compositions, adhesives and sealants, and also as raw materials in the preparation of polyisocyanates containing isocyanate groups, especially prepolymers, and also for the synthesis of polyurethane dispersions and polyurethane solutions.

Polyisocyanate mixtures having allophanate groups are known and are described, for example, in U.S. Pat. No. 3,769, 318, GB-A 994 890 or EP-A 0 666 276. Although diphenylmethane 4,4'-diisocyanate is mentioned as suitable starting material, that publication does not give any indication as to whether and under what conditions liquid, crystallization-stable polyisocyanate mixtures can be prepared by modifying diphenylmethane 2,4'-diisocyanate.

As well as diphenylmethane 2,4'-diisocyanate, monohydric alcohols having 3 to 18 carbon atoms per molecule are starting materials for the process according to the invention. Preference is given to linear, i.e. unbranched, monohydric aliphatic alcohols which are liquid at room temperature and have 3 to 10 carbon atoms. Mixtures of different alcohols of this kind can of course likewise be used.

Suitable alcohols are, for example, n-propanol, isopropanol, n-butanol, isobutanol, n-pentanol, n-hexanol, n-octanol, 2-ethylhexanol, n-decanol, n-dodecanol, n-hexadecanol, and also alcohols containing ether groups, the monohydric alcohols obtained by ethoxylating or propoxylating the simple alkanols mentioned by way of example, for example ethylene glycol monomethyl ether, ethylene glycol monoethyl ether, ethylene glycol monobutyl ether, ethylene glycol monoisopropyl ether, diethylene glycol monobutyl ether. Preference is given to monoalcohols free of ether groups.

The allophanatization is effected, at least after the intermediate urethane formation, in the presence of catalysts which promote allophanatization. Suitable catalysts are, for example, metal compounds of main groups 3 and 4 and also transition groups 1, 2, 6, 7 and 8 which are soluble in the reaction mixture and are of the type specified in U.S. Pat. No. 3,769,318. Particular preference is given to using tin(II) octoate or zinc acetylacetonate in amounts of 20 to 2000 ppm (weight), preferably 20 to 200 ppm (weight), based on the reaction mixture. In contrast to the recommendation of U.S. Pat. No. 3,769,318, presence of alkylating compounds during the reaction is not required. The inventive polyisocyanate mixtures contain exclusively allophanate structures and no urethane structures, isocyanurate structures and/or carbodiimide structures. This is demonstrated unambiguously by 13C NMR spectroscopy studies.

The process according to the invention is performed at temperatures of up to 160° C. The preferred temperature for the allophanatization is 80 to 120° C. In a preferred method, the inventive polyisocyanate mixtures are prepared in 2-stage procedure. In a first process step, molten diphenylmethane 2,4'-diisocyanate is initially charged and the monoalcohol is added dropwise at a temperature between 40 and 80° C., preferably between 50 and 70° C. In the second process step, on attainment of the NCO content calculated for the urethane formation, the catalyst is added and then the temperature is increased to 80 to 160° C., preferably to 80 to 120° C. The reaction is then terminated on attainment of the NCO content calculated for the allophanatization, preferably by adding a catalyst poison. Suitable catalyst poisons are, for example, alkylating or acylating compounds, for example methyl p-toluenesulphonate, dimethyl sulphate, benzoyl chloride or isophthaloyl chloride, which are preferably used in at least equimolar amounts, based on the amount of catalyst used.

The inventive polyisocyanate mixtures are almost colourless to dark yellow-coloured liquid mixtures with low viscosities between 200 and 80 000 mPa·s (23° C.), viscosity increasing as the amount of allophanate structures rises. It is found that the viscosities are surprisingly lower than those of the corresponding 4,4'-MDI allophanates. This is very surprising because the viscosity of pure 2,4'-MDI at 40° C. of 11.0 mPa·s is higher than that of pure 4,4'-MDI (4.1 mPa·s). The NCO content of the inventive polyisocyanate mixtures is 14 to 24% by weight.

Compared to corresponding mixtures based on diphenylmethane 4,4'-diisocyanate, the inventive polyisocyanate mixtures exhibit an improved crystallization stability at low temperatures, for example at below 5° C. Product mixtures with a high degree of allophanatization exhibit good crystallization stability even at temperatures below −5° C.

The inventive polyisocyanate mixtures are suitable starting compounds for preparing polyurethanes in general. However, the mixtures are preferably used to prepare solvent-free polyurethane coatings, polyurethane sealants and polyurethane adhesives, for polyurea coatings and for the synthesis of polyurethane dispersions and polyurethane solutions. To prepare these products, the inventive polyisocyanate mixtures are combined and reacted with solvent-free polyhydroxyl compounds known per se from polyurethane chemistry or mixtures thereof, the quantitative ratios of the individual components preferably corresponding to an NCO/OH equivalents ratio of 0.8:1 to 5:1, preferably 0.8:1 to 3:1 and more preferably 0.8:1 to 1.5:1. Suitable polyhydroxyl compounds are, for example, polyetherpolyols, polyesterpolyols, polyacrylatepolyols and polycarbonatepolyols. In order to ensure bubble-free hardening in the case of coating applications with high layer thicknesses, the inventive polyisocyanate mixtures are preferably combined with castor oil or blends of castor oil with ketone-formaldehyde resins and/or polyesterpolyols and/or polyetherpolyols and/or polycarbonatepolyols. Such prepolymers based on 2,4'-MDI allophanates are notable for better storage stability and a longer processing time compared to systems based on 4,4'-MDI.

A further field of application is that of polyurethane dispersions in which the 2,4'-MDI allophanates, owing to their lower reactivity compared to 4,4'-allophanates, are less susceptible to undesired side reactions, for example with carboxylic acid groups and water.

For adhesive and sealant applications, the inventive polyisocyanate mixtures are preferably combined with polyesterpolyols and/or polyetherpolyols. In the case of the preparation of aqueous polyurethane dispersions based on the inventive polyisocyanate mixtures, preference is given to using polyesterpolyols and/or polycarbonatepolyols as reactants.

Polyacrylatepolyols are preferred as reactants for the inventive polyisocyanate mixtures when coating applications with low layer thicknesses and rapid physical drying are required.

Addition of pigments and other assistants and additives, such as fillers, levelling aids, is required for most applications and is preferably undertaken by mixing these additives into one of the starting components. The products comprising the inventive polyisocyanate mixtures can be applied in one or more layers to any desired substrates by the customary known methods, for example by spraying, spreading, dipping, flow-coating, or with the aid of rollers or doctor blades.

Suitable substrates are, for example, metal, wood, glass, stone, ceramic materials, concrete, rigid and flexible plastics, textiles, leather or paper. The substrates can be provided with the customary primers before the application process.

The examples which follow serve to further illustrate the invention. All percentages are based on weights. The diphenylmethane 2,4'-diisocyanate used in the examples which follow is a technical grade product with of 99.25% by weight content of the 2,4'-isomer.

All the references described above are incorporated by reference in its entirety for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

Example 1

Preparation of an Inventive Polyisocyanate Mixture 931 g of molten diphenylmethane 2,4'-diisocyanate are initially charged under a nitrogen atmosphere in a 2 liter three-neck flask with stirrer, reflux condenser and dropping funnel, and heated to 60° C. At this temperature, 69 g of n-butanol (NCO/OH ratio 8:1) are added dropwise within 20 minutes. The mixture is then stirred at 60° C. until the isocyanate content of 27.4% calculated for urethane formation has been attained. 0.1 g of zinc acetylacetonate is then added and the temperature is increased to 100° C. The mixture is stirred at this temperature until the NCO content of 23.5% calculated for allophanate formation has been attained. The reaction is then ended by adding 0.1 g of benzoyl chloride. The mixture is then cooled to 30° C. A clear, yellowish-coloured polyisocyanate mixture having a viscosity of 250 mPa·s (23° C.) is obtained. The product is crystallization-stable at a temperature of 0° C. for 2 weeks; at a temperature of −10° C., the product becomes cloudy after approx. 6 days. The product contains a calculated 9.4 content of allophanate groups.

Example 2

Preparation of an Inventive Polyisocyanate Mixture 9218 g of molten diphenylmethane 2,4'-diisocyanate are initially charged under a nitrogen atmosphere in a 15 liter metal reactor with stirrer, reflux condenser and dropping funnel, and heated to 60° C. At this temperature, 780 g of n-butanol (NCO/OH ratio 7:1) are added dropwise within 20 minutes. The mixture is then stirred at 60° C. until the isocyanate content of 26.5% calculated for urethane formation has been attained. 1.0 g of zinc acetylacetonate is then added and the temperature is increased to 100° C. The mixture is stirred at this temperature until the NCO content of 22.1% calculated for allophanate formation has been attained. The reaction is then ended by adding 1.0 g of benzoyl chloride. The mixture is then cooled to 30° C. A clear, yellowish-coloured polyisocyanate mixture having a viscosity of 795 mPa·s (23° C.) is obtained. The product is crystallization-stable at a temperature of 0° C. for 3 weeks; at a temperature of −10° C., the product becomes cloudy after approx. 10 days. The product contains a calculated 10.6% content of allophanate groups.

Example 3

Preparation of an Inventive Polyisocyanate Mixture 9100 g of molten diphenylmethane 2,4'-diisocyanate are initially charged under a nitrogen atmosphere in a 15 liter metal reactor with stirrer, reflux condenser and dropping funnel, and heated to 60° C. At this temperature, 898 g of n-butanol (NCO/OH ratio 6:1) are added dropwise within 20 minutes. The mixture is then stirred at 60° C. until the isocyanate content of 25.5% calculated for urethane formation has been attained. 1.0 g of zinc acetylacetonate is then added and the temperature is increased to 100° C. The mixture is stirred at this temperature until the NCO content of 20.4% calculated for allophanate formation has been attained. The reaction is then ended by adding 1.0 g of benzoyl chloride. The mixture is then cooled to 30° C. A clear, yellowish-coloured polyisocyanate mixture having a viscosity of 2930 mPa·s (23° C.) is obtained. The product is crystallization-stable at a temperature of 0° C. for 4 weeks; at a temperature of −10° C., the product becomes cloudy after approx. 15 days. The product contains a calculated 12.2% content of allophanate groups.

Example 4

Preparation of an Inventive Polyisocyanate Mixture 871 g of molten diphenylmethane 2,4'-diisocyanate are initially charged under a nitrogen atmosphere in a 2 liter three-neck flask with stirrer, reflux condenser and dropping funnel, and heated to 60° C. At this temperature, 129 g of n-butanol (NCO/OH ratio 4:1) are added dropwise within 20 minutes. The mixture is then stirred at 60° C. until the isocyanate content 21.9% calculated for urethane formation of has been attained. 0.2 g of zinc acetylacetonate is then added and the temperature is increased to 100° C. The mixture is stirred at this temperature until the NCO content of 14.6% calculated for allophanate formation has been attained. The reaction is then ended by adding 0.2 g of benzoyl chloride. The mixture is then cooled to 30° C. A clear, yellowish-coloured polyisocyanate mixture having a viscosity of 71550 mPa·s (23° C.) is obtained. The product is crystallization-stable at a temperature of 0° C. for 2 months; at a temperature of −10° C., the product becomes cloudy after approx. 3 weeks. The product contains a calculated 17.6% content of allophanate groups.

Example 5

Preparation of an Inventive Polyisocyanate Mixture 943 g of molten diphenylmethane 2,4'-diisocyanate are initially charged under a nitrogen atmosphere in a 2 liter three-neck flask with stirrer, reflux condenser and dropping funnel, and heated to 60° C. At this temperature, 57 g of 2-propanol (NCO/OH ratio 8:1) are added dropwise within 20 minutes. The mixture is then stirred at 60° C. until the isocyanate content of 27.7% calculated for urethane formation of has been attained. 0.1 g of zinc acetylacetonate is then added and the temperature is increased to 100° C. The mixture is stirred at this temperature until the NCO content of 23.7% calculated for allophanate formation of has been attained. The reaction is then ended by adding 0.1 g of benzoyl chloride. The mixture is then cooled to 30° C. A clear, yellowish-coloured polyisocyanate mixture having a viscosity of 718 mPa·s (23° C.) is obtained. The product is crystallization-stable at a temperature of 0° C. for 2 weeks; at a temperature of −10° C., the product becomes cloudy after approx. 6 days. The product contains a calculated 9.5% content of allophanate groups.

Example 6

Preparation of an Inventive Polyisocyanate Mixture 894 g of molten diphenylmethane 2,4'-diisocyanate are initially charged under a nitrogen atmosphere in a 2 liter three-neck flask with stirrer, reflux condenser and dropping funnels and heated to 60° C. At this temperature, 106 g of n-butanol (NCO/OH ratio 5:1) are added dropwise within 20 minutes. The mixture is then stirred at 60° C. until the isocyanate content of 24.0% calculated for urethane formation of has been attained. 0.2 g of zinc acetylacetonate is then added and the temperature is increased to 100° C. The mixture is stirred at this temperature until the NCO content of 18.0% calculated for allophanate formation has been attained. The reaction is then ended by adding 0.2 g of benzoyl chloride. The mixture is then cooled to 30° C. A clear, yellowish-coloured polyisocyanate mixture having a viscosity of 6580 mPa·s (23° C.) is obtained. The product is crystallization-stable at a temperature of 0° C. for 2 months; at a temperature of −10° C., the product becomes cloudy after approx. 3 weeks. The product contains a calculated 14.4% content of allophanate groups.

The invention claimed is:

1. A polyisocyanate mixture which is liquid at temperatures above −5° C. and is based on diphenylmethane 2,4'-diisocyanate, wherein
   A) the NCO content of said polyisocyanate mixture is 14.5 to 24% by weight;
   B) the content of isocyanate groups bonded in the 2 position of said polyisocyanate mixture is greater than 50%; and
   C) the content of allophanate groups (calculated as $C_2HN_2O_3$ having a molecular weight of 101) of said polyisocyanate mixture is 7.7 to 17.6% by weight
   wherein said diphenylmethane 2,4'-diisocyanate is pure 2,4'- isomer or a mixture of 2,4'- isomer with up to 2.0% by weight of diphenylmethane 4,4'-diisocyanate and/or up to 1.0% by weight of diphenylmethane 2,2'-diisocyanate, based on the total weight of said polyisocyanate mixture and
   wherein said polyisocyanate mixture comprises reaction products prepared with intermediate urethane formation from
   A) diphenylmethane 2,4'-diisocyanate with
   B) monohydric alcohols having 3 to 18 carbon atoms per molecule while maintaining an NCO/OH ratio of 4:1 to 8.5:1.

2. The polyisocyanate mixture of claim 1, wherein said polyisocyanate mixture comprises reaction products prepared with intermediate urethane formation from A) diphenylmethane 2,4'-diisocyanate with B) linear, monohydric alcohols having 4 to 10 carbon atoms.

3. A process for preparing a polyisocyanate mixture which is liquid at temperatures between −5 and +5° C. and are based on diphenylmethane 2,4'-diisocyanate, wherein said diphenylmethane 2,4'-diisocyanate is pure 2,4'- isomer or a mixture of 2,4'- isomer with up to 2.0% by weight of diphenylmethane 4,4'-diisocyanate and/or up to 1.0% by weight of diphenylmethane 2,2'-diisocyanate, based on the total weight of said polyisocyanate mixture, comprising reacting said diphenylmethane 2,4'-diisocyanate with monohydric alcohols having 3 to 18 carbon atoms per molecule while maintaining an NCO/OH ratio of 4:1 to 8.5:1 at temperatures up to 160° C. with intermediate urethane formation, wherein said reaction is carried out no later than after completion of urethane formation in the presence of a catalyst which promotes allophanate formation.

4. The process of claim 3, wherein said catalyst comprises a compound of the third or fourth main group or of transition group 1, 2, 6, 7 or 8 of the Periodic Table of the Elements, and which are soluble in the reaction mixture.

5. The process of claim 4, wherein said catalyst used comprises tin (II) octoate or zinc acetylacetonate.

6. An isocyanate-functional prepolymer, a polyurethane dispersion, a polyurethane solution, or a silane-terminated prepolymer comprising the polyisocyanate mixture of claim 1 as polyisocyanate component.

7. An isocyanate-functional prepolymer, a polyurethane dispersion, a polyurethane solution, or a silane-terminated prepolymer comprising the polyisocyanate mixture of claim 2 as polyisocyanate component.

8. A single- or two-component polyurethane coating composition comprising the polyisocyanate mixture of claim 1 as polyisocyanate component.

9. A single- or two-component polyurethane coating composition comprising the polyisocyanate mixture of claim 2 as polyisocyanate component.

10. An adhesive comprising a compound obtained from the polyisocyanate mixture of claim 1.

11. An adhesive comprising a compound obtained from the polyisocyanate mixture of claim 2.

12. A sealant comprising a compound obtained from the polyisocyanate mixture of claim 1.

13. A sealant comprising a compound obtained from the polyisocyanate mixture of claim 2.

* * * * *